United States Patent
Weissmüller et al.

[11] Patent Number: 4,829,063
[45] Date of Patent: May 9, 1989

[54] SACCHARINE SALTS OF SUBSTITUTED AMINES

[75] Inventors: Joachim Weissmüller, Monheim; Stefan Dutzmann, Duesseldorf; Paul Reinecke, Leverkusen, all of Fed. Rep. of Germany

[73] Assignee: Bayer Aktiengesellschaft, Leverkusen, Fed. Rep. of Germany

[21] Appl. No.: 118,107

[22] Filed: Nov. 5, 1987

[30] Foreign Application Priority Data

Nov. 22, 1986 [DE] Fed. Rep. of Germany ....... 3639901

[51] Int. Cl.$^4$ ..................... A61K 31/39; C07D 275/06
[52] U.S. Cl. .................................. 514/229.2; 514/373; 514/321; 514/212; 514/229.5; 540/484; 544/109; 546/198; 548/211
[58] Field of Search ........................ 540/484; 544/109; 546/198; 548/211; 514/373, 321, 229.5, 229.2, 212

[56] References Cited

U.S. PATENT DOCUMENTS 4,721,786  1/1958  Weissmuller et al. ................... 71/88

FOREIGN PATENT DOCUMENTS 49-117627  3/1973  Japan .................................. 514/373

OTHER PUBLICATIONS

Chemical Abstracts vol 104, (1986), Item 2022995, (Abstracting German Offenlegungsshrift DE 3,430,805, 8 Mar. 1984, 49 pages).

Chemical abstracts, vol. 79 (1973), Item 88317y (abstracting Japanese Kokai 73/33,026, 7 May 1973, 4 pages).

Primary Examiner—Robert T. Bond
Attorney, Agent, or Firm—Sprung, Horn, Kramer & Woods

[57] ABSTRACT

Fungicidally active novel saccharine salts of substituted amines of the formula

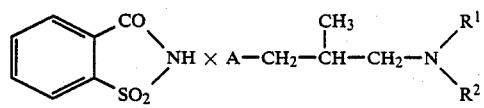

in which
A represents in each case optionally substituted 2-decahydronaphthyl or β-naphthyl and
$R^1$ and $R^2$ independently of one another in each case represent alkyl or alkenyl or, together with the nitrogen atom to which they are bonded, represent an optionally substituted saturated heterocyclic radical, which can contain further heteroatoms.

8 Claims, No Drawings

SACCHARINE SALTS OF SUBSTITUTED AMINES

The invention relates to new saccharine salts of substituted amines, a process for their preparation and their use as agents for combating pests.

It is already known that saccharine salts of amines, such as, for example, the saccharine salt of 5-amino-1,2,4-triazole or the saccharine salt of cyclohexylamine, have fungicidal properties (compare European Pat. No. 158,074).

However, the action of these already known compounds is not completely satisfactory in all fields of use, especially when low amounts are applied and in the case of low concentrations.

New saccharine salts of substituted amines of the general formula (I)

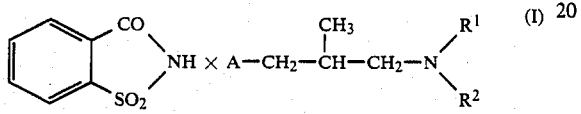

in which
A represents in each case optionally substituted 2-decahydronaphthyl or β-naphthyl and
$R^1$ and $R^2$ independently of one another in each case represent alkyl or alkenyl or, together with the nitrogen atom to which they are bonded, represent an optionally substituted saturated heterocyclic radical, which can contain further heteroatoms, have been found.

The compounds of the formula (I) can be in the form of geometric and/or optical isomers or isomer mixtures of varying composition. Both the pure isomers and the isomer mixtures are within the present invention.

It has furthermore been found that the new saccharine salts of substituted amines of the general formula (I)

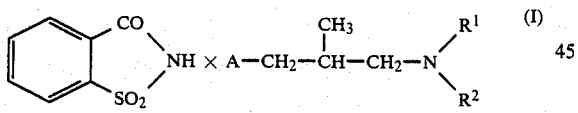

in which
A represents in each case optionally substituted 2-decahydronaphthyl or β-naphthyl and
$R^1$ and $R^2$ independently of one another in each case represent alkyl or alkenyl or, together with the nitrogen atom to which they are bonded, represent an optionally substituted saturated heterocyclic radical, which can contain further heretoatoms,
are obtained by a process in which substituted amines of the formula (II)

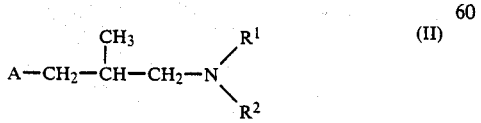

in which A, $R^1$ and $R^2$ have the abovementioned meaning, are reacted with saccharine, if appropriate in the presence of a diluent.

Finally, it has been found that the new saccharine salts of substituted amines of the general formula (I) have an action against pests.

Surprisingly, the saccharine salts of substituted amines of the general formula (I) according to the invention show, for example, a better fungicidal activity than the amine saccharine salts known from the prior art, such as, for example, the saccharine salt of 5-amino-1,2,4-triazole or the saccharine salt of cyclohexylamine, which are closely related compounds chemically and from the point of view of their action.

Formula (I) provides a general definition of the saccharine salts of substituted amines according to the invention. Preferred salts of the formula (I) are those in which
A represents 2-decahydronaphthyl which is optionally mono-, di- or trisubstituted by identical or different substituents, substituents which may be mentioned being: hydroxyl and in each case straight-chain or branched alkyl and alkoxy with in each case 1 to 6 carbon atoms; or furthermore represents β-naphthyl which is optionally mono-, di- or trisubstituted by identical or different substituents, substituents which may be mentioned being: halogen, hydroxyl and in each case straight-chain or branched alkyl and alkoxy with in each case 1 to 6 carbon atoms,
$R^1$ and $R^2$ independently of one another represent in each case straight-chain or branched alkyl or alkenyl with in each case up to 6 carbon atoms or, together with the nitrogen atom to which they are bonded, represent a saturated 5- to 7-membered heterocyclic radical which is optionally mono-, di- or trisubstituted by identical or different substituents and can contain 1 or 2 further heteroatoms, in particular nitrogen or oxygen, substituents which may be mentioned in each case being: in each case straight-chain or branched alkyl and hydroxyalkyl with in each case 1 to 4 carbon atoms. Particularly preferred salts of the formula (I)
are those
in which
A represents 2-decahydronaphthyl which is optionally mono- or disubstituted by identical or different substituents, substituents which may be mentioned in each case being: methyl, ethyl, n- or i-propyl, n-, i-, s- or t-butyl, 2-methyl-but-2-yl, methoxy and ethoxy; or furthermore represents β-naphthyl which is optionally mono-, di- or trisubstituted by identical or different substituents, substituents which may be mentioned being: fluorine, chlorine, bromine, methyl, ethyl, n- or i-propyl, n-, i-, s- or t-butyl, 2-methyl-but-2-yl, methoxy and ethoxy,
$R^1$ and $R^2$ independently of one another in each case represent methyl, ethyl, n- or i-propyl, allyl, butenyl, dimethylallyl, n- or i-butyl or n- or i-pentenyl or, together with the nitrogen atom to which they are bonded, represent a heterocyclic radical of the formula

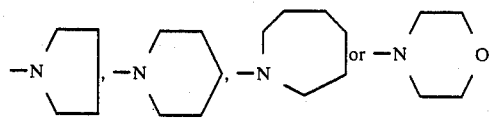

which is optionally mono-, di- or trisubstituted by identical or different substituents, possible substituents being: methyl, ethyl and hydroxymethyl.
The following salts of the general formula (I) may be mentioned specifically in addition to the compounds mentioned in the preparation examples:
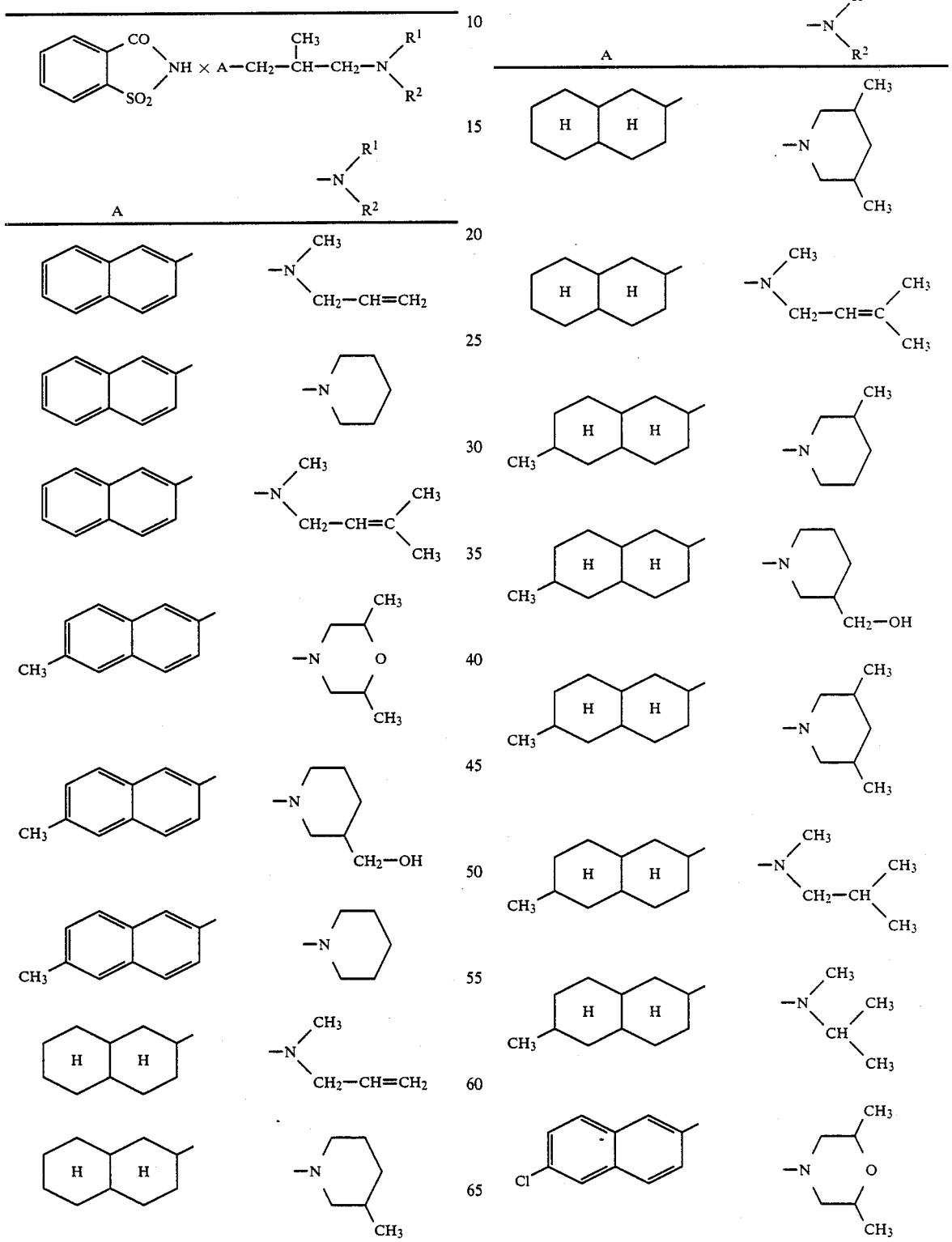

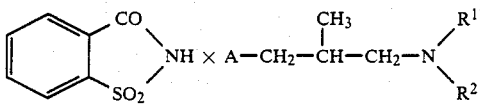

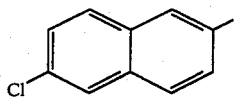

If, for example, 1-β-naphthyl-2-methyl-3-(3-methyl-piperidin-1-yl)-propane and saccharine are used as starting substances, the course of the reaction in the process according to the invention can be represented by the following equation:

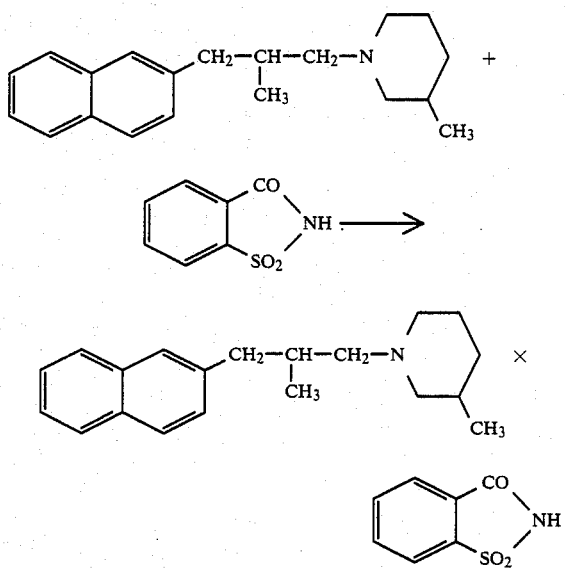

Formula (II) provides a general definition of the substituted amines required as starting substances for carrying out the process according to the invention. In this formula (II) A, R¹ and R² represent those radicals which have already been mentioned for these substituents in connection with the description of the substances of the formula (I) according to the invention.

The substituted amines of the formula (II) are known in some cases (compare DE-OS (German Published Specification) No. 3,413,897).

Substituted amines of the formula (IIa)

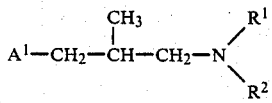 (IIa)

in which
A¹ represents optionally substituted 2-decahydronaphthyl and
R¹ and R² have the abovementioned meaning are the subject of Application Ser. No. 070,854, filed July 8, 1987, now pending corresponding to German patent application No. P 3,624,648 of July 22, 1986 and they are obtainable, for example, by a process in which the known substituted amines of the formula (IIb)

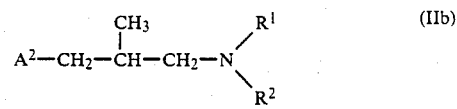 (IIb)

in which
A² represents optionally substituted β-naphthyl and
R¹ and R² have the abovementioned meaning,
are hydrogenated in the customary manner with hydrogen in the presence of a catalyst, such as, for example, ruthenium on carbon, if appropriate in the presence of a diluent, such as, for example, tetrahydrofuran, in a pressure range between 1 and 300 atmospheres and at a temperature between 20° C. and 250° C.

Possible diluents for carrying out the process according to the invention are inert organic solvents.

These include, in particular, ethers, such as diethyl ether, dioxane, tetrahydrofuran or ethylene glycol dimethyl or diethyl ether; ketones, such as acetone or butanone; nitriles, such as acetonitrile or propionitrile; amides, such as dimethylformamide, dimethylacetamide, N-methylformanilide, N-methylpyrrolidone or hexamethylphosphoric acid triamide, or alcohols, such as methanol, ethanol or propanol.

The reaction temperatures can be varied within a substantial range in carrying out the process according to the invention. The reaction is in general carried out at temperatures between 0° C. and 100° C., preferably at temperatures between 10° C. and 50° C.

For carrying out the process according to the invention, equimolar amounts of saccharine are added per mole of substituted amine of the formula (II). The two reaction partners are dissolved in a suitable solvent at the suitable reaction temperature and the solvent is then removed by distillation in vacuo. The salts thus obtainable, which occasionally are obtained as viscous oils or in amorphous form, can be purified by generally customary processes, such as, for example, by recrystallization or digestion in suitable solvents. In these cases, they are characterized with the aid of spectroscopic methods (IR; NMR).

The active compounds according to the invention have a powerful action against pests and can be used in practice for combating undesirable harmful organisms. The active compounds are suitable for use as plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some caustic organisms of fungal diseases which come under the generic names listed above may be mentioned as examples, but not by way of Limitation: Pythium species, such as, for example, *Pythium ultimum;* Phytophthora species, such as, for example, *Phytophthora infestans;* Pseudoperonospora species, such as, for example, *Pseudoperonospora humuli* or *Pseudoperonospora cubensis;* Plasmopara species, such as, for example, *Plasmopara viticola;* Peronospora species, such as, for example, *Peronospora pisi* or *P. brassicae;* Erysiphe species, such as, for example, *Erysiphe graminis;* Sphaerotheca species, such as, for example, *Sphaerotheca fuliginea;* Podosphaera species, such as, for example, *Podosphaera leucotricha;* Venturia species, such as, for example, *Venturia inaequalis;* Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus;* Puccinia species, such as, for example, *Puccinia recondita;* Tilletia species, such as, for example, *Tilletia caries;* Ustilago species, such as, for example, *Ustilago nuda* or *Ustilago avenae;* Pellicularia species, such as, for example, *Pellicularia sasakii;* Pyricularia species, such as, for example, *Pyricularia oryzae;* Fusarium species, such as, for example, *Fusarium culmorum;* Botyrtis species, such as, for example, *Botyrtis cinerea;* Septoria species, such as, for example, *Septoria nodorium;* Leptosphaeria species, such as, for example, *Leptosphaeria nodorum;* Cercospora species, such as, for example, *Cercospora canescens;* Alternaria species, such as, for example, *Alternaria brassicae* and Pseudocercosporella species, such as, for example, Pi Pseudocercosporella herpotrichoides.

The good toleration, by plants, of the active compounds, at the concentrations required for combating plant diseases, permits treatment of above-ground parts of plants, of vegetative propagation stock and seeds, and of the soil.

The active compounds according to the invention can thereby be employed with particularly good success for combating cereal diseases, such as, for example, against the powdery mildew of cereals causative organism (*Erysiphe graminis*), against the leaf spot disease on cereals causative organism (*Pyrenophora teres*), against the brown spot of wheat causative organism (*Septoria nodorum*), against Oomycetes species and against the rice spot disease causative organism (*Pyricularia oryzae*). It should be emphasized that the active compounds according to the invention also have systemic properties, as well as a good protective activity.

Depending on their particular physical and/or chemical properties, the active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and furthermore in formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, and in mixtures with fertilizers and growth regulators.

The active compounds can be used as such or in the form of their formulations or the use forms prepared therefrom by further dilution, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

Example 1

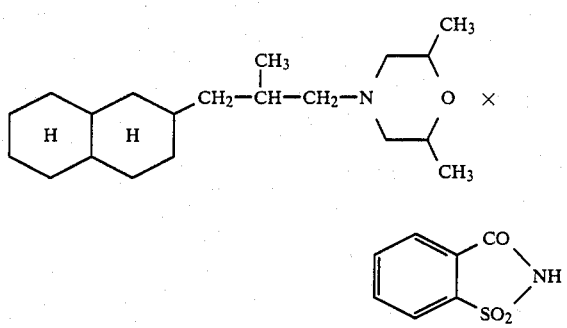

4.5 g (0.014 mol) of 1-(2,6-dimethylmorpholin-4-yl)-2-methyl-3-(decahydronaphth-2-yl)-propane and 2.58 g (0.014 mol) of saccharine are dissolved together in 80 ml of acetone and the solution is stirred at room temperature for 15 minutes. After the solvent has been evaporated off, 7 g (100% of theory) of 1-(2,6-dimethylmorpholin-4-yl)-2-methyl-3-(decahydronaphth-2-yl)-propane saccharine salt are obtained as an amorphous solid.

$^1$H-NMR: $\delta$=7.6 (m, 2H); 7.8 (m, 2H); 4.2–4.4 (m, 2H); 3.55–3.75 (m, 2H); 3.0–3.1 (m, 1H); 2.85–2.95 (m, 1H); 2.3–2.5 (m, 2H); 2.1–2.2 (m, 1H); 0.8–1.8 (m, 28H) ppm.

EXAMPLE 2

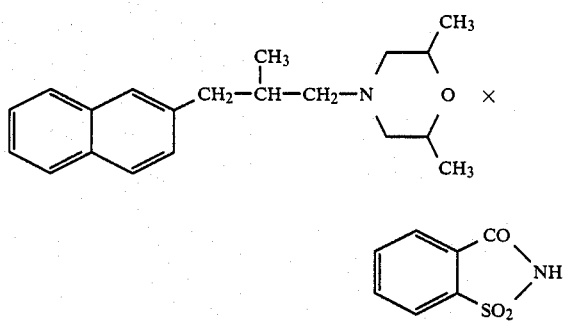

A solution of 3.23 g (0.0176 mol) of saccharine in 50 ml of ethanol is added to a solution of 5.24 g (0.0176 mol) of 1-(2,6-dimethylmorpholin-4-yl)-2-methyl-3-$\beta$-naphthyl-propane in 40 ml of ethanol, the mixture is stirred at room temperature for 10 minutes and the solvent is removed in vacuo.

8.47 g (100% of theory) of 1-(2,6-dimethylmorpholin-4-yl)-2-methyl-3-$\beta$-naphthyl-propane saccharine salt are obtained as an amorphous solid.

$^1$H-NMR, $\delta$=7.2–8.0 (m, 11H); 4.2–4.4 (m, 2H); 3.4–3.7 (m, 2H); 3.1–3.2 (m, 1H); 2.8–3.0 (m, 2H); 2.1–2.6 (m, 2H); 0.6–1.6 (m, 12H) ppm.

Preparation of the Starting Compounds

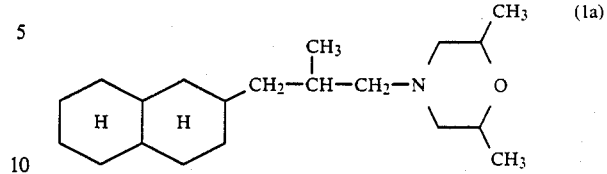

10 g (0.033 mol) of 1-(2,6-dimethylmorpholin-4-yl)-2-methyl-3-$\beta$-naphthyl-propane are hydrogenated in 150 ml of tetrahydrofuran at 120° C. in the presence of 3 g of ruthenium-on-carbon (5%) under a hydrogen pressure of 150 bar for 3 hours. The catalyst is filtered off and the solvent is evaporated in vacuo.

7.7 g (74.6% of theory) of 1-(2,6-dimethylmorpholin-4-yl)-2-methyl-3-(decahydronaphth-2-yl)-propane of reactive index $n_D^{20}$=1.4869 are obtained.

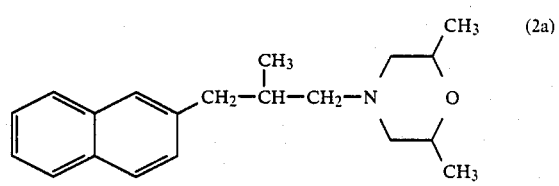

10.8 g (0.04 mol) of 1-methanesulphonyl-2-methyl-3-$\beta$-naphthylpropane and 9 g (0.078 mol) of 2,6-dimethylmorpholine are stirred at a bath temperature of 140° C. for 15 hours. Water is added to the resulting reaction mixture and the mixture is extracted several times with ether. The combined organic phases are dried over sodium sulphate and freed from the solvent in vacuo; the oily residue is purified by column chromatography (silica gel 60, petroleum ether/ethyl acetate=2:1). 6.2 g (52% of theory) of 1-(2,6-dimethylmorpholin-4-yl)-2-methyl-3-$\beta$-naphthyl-propane of refractive index $n_D^{20}$=1.5527 are obtained.

Preparation of the Starting Substance for the Preparation of 2a

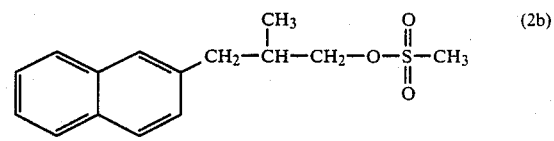

11 g (0.1 mol) of methanesulphonyl chloride are added dropwise to 14 g (0.074 mol) of 2-methyl-3-$\beta$-naphthylpropanol (crude) in 80 ml of absolute pyridine at 0° C., with stirring, the mixture is stirred at room temperature for a further 16 hours. When the addition has ended, excess pyridine is removed by distillation in vacuo, the residue is taken up in water, the mixture is extracted several times with methylene chloride, the extract is dried over sodium sulphate and the solvent is removed in vacuo. 13.6 g (66% of theory) of 1-methanesulphonyloxy-2-methyl-3-$\beta$-naphthyl-propane are obtained as an oil.

(IR: $\nu$=1345, 1180 cm$^{-1}$).

Preparation of the Starting Substance for the Preparation of 2b

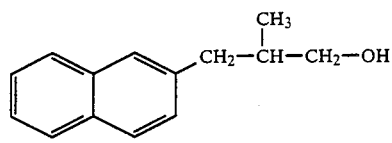 (2c)

12 g (0.05 mol) of ethyl 2-methyl-3-β-naphthylacrylate are added dropwise to a suspension of 1.9 g (0.05 mol) of lithium aluminum hydride in 150 ml of absolute ether in a dry nitrogen atmosphere, while cooling with ice. When the addition has ended, the mixture is heated at the reflux temperature for 8 hours and, after the reaction mixture has cooled, 15 ml of 5% strength sulphuric acid are then slowly added dropwise, with cooling, the solid which has precipitated is filtered off with suction, the filtrate is dried over sodium sulphate, the solvent is removed in vacuo and the residue is recrystallized from ether/petroleum ether. 7.1 g of 2-methyl-3-β-naphthyl-propanol of melting point 71°-74° C., which, according to the gas chromatogram, is contaminated with 2-methyl-1-β-naphthyl-propen-3-ol and can be used in the next reaction stage without further purification, are obtained.

Preparation of the Starting Substance for the Preparation of 2c

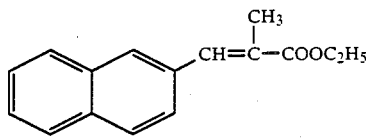 (2d)

40 g (0.2 mol) of ethyl α-ethoxalylpropionate are added to a suspension of 5.5 g (0.2 mol) of 80% strength sodium hydride in 300 ml of absolute xylene at 70° C. When the evolution of hydrogen has ended, 31.2 g (0.2 mol) of β-naphthaldehyde, dissolved in xylene, are added dropwise, and when the addition has ended the mixture is heated at the boiling point for 90 minutes. 150 ml of water are added to the cooled reaction mixture and the organic phase is separated off, washed with 7% strength sodium carbonate solution, dried over sodium sulphate and concentrated. The residue is distilled in vacuo. 21.7 g (45.2% of theory) of ethyl 2-methyl-3-β-naphthyl-acrylate of boiling point 110° C./0.13 mbar are obtained.

The following saccharine salts of substituted amines of the general formula (I) are obtained in a corresponding manner and in accordance with the general statements on the preparation:

$$\text{(I)}$$

| Example No. | A | $-N\begin{matrix}R^1\\R^2\end{matrix}$ | Physical data |
|---|---|---|---|
| 3 | 2-naphthyl | 3-methylpiperidinyl | Mp 42° C. |
| 4 | 2-naphthyl | 3,5-dimethylpiperidinyl | $^1$H—NMR*: 3.3–3.7; 3.0–3.2; 2.5–3.0; 2.2–2.5; |
| 5 | methyl-decalinyl | 3,5-dimethylmorpholinyl | Mp 53° C.–56° C. |
| 6 | methyl-decalinyl | piperidinyl | Mp 36° C. |

-continued $$\underset{SO_2}{\underset{CO}{\bigcirc}} NH \times A-CH_2-\underset{CH_3}{\overset{|}{CH}}-CH_2-N\underset{R^2}{\overset{R^1}{\diagdown}} \quad (I)$$

| Example No. | A | $-N\overset{R^1}{\underset{R^2}{\diagdown}}$ | Physical data |
|---|---|---|---|
| 7 | 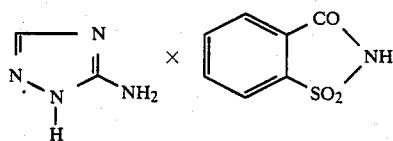 | 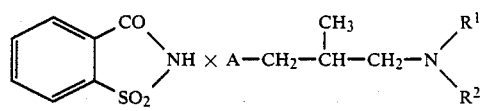 | $^1$H—NMR*: 3.3–3.7; 3.0–3.2; 2.6–3.0; |
| 8 | 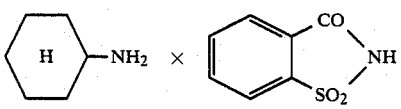 | | Mp 34° C. |

*The $^1$H—NMR spectra were recorded in CDCl$_3$ with tetramethylsilane (TMS) as the internal standard.

The chemical shift is stated as the δ value in ppm.

USE EXAMPLES

The compounds shown below were employed as comparison substances in the use examples which follow:

(A)

Saccharine salt of 5-amino-1,2,4-triazole and (B)

saccharine salt of cyclohexylamine (both known from European Pat. No. 158,074).

EXAMPLE A

Erysiphe test (barley)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of *Erysiphe graminis* f.sp. hordei.

The plants are placed in a greenhouse at a temperature of about 20° C. and a relative atmospheric humidity of about 80%, in order to promote the development of powdery mildew pustules.

Evaluation is carried out 7 days after the inoculation.

In this test, a clearly superior activity compared with the prior art is shown, for example, by the compounds according to Preparation Examples 2, 3 and 4.

It is understood that the specification and examples are illustrative but not limitative of the present invention and that other embodiments within the spirit and scope of the invention will suggest themselves to those skilled in the art.

We claim:

1. A saccharine salt of a substituted amine of the formula $$\underset{SO_2}{\underset{CO}{\bigcirc}} NH \times A-CH_2-\underset{CH_3}{\overset{|}{CH}}-CH_2-N\underset{R^2}{\overset{R^1}{\diagdown}}$$

in which

A represents 2-decahydronaphthyl which is optionally mono-, di- or trisubstituted by substituents independently selected from the group consisting of hydroxyl and in each case straight-chain or branched alkyl and alkoxy with in each case 1 to 6 carbon atoms; or furthermore represents β-naphthyl which is optionally mono-, di- or trisubstituted by substituents selected from the group consisting of halogen, hydroxyl and in each case straight-chain or branched alkyl and alkoxy with in each case 1 to 6 carbon atoms, and R$^1$ and R$^2$ independently of one another in each case represent methyl, ethyl, n- or i-propyl, allyl, butenyl, dimethylallyl, n- or i-butyl or n- or i-pentenyl or, together with the nitrogen atom to which they are bonded, represent a heterocyclic radical of the formula

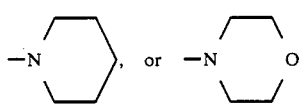

which is optionally mono-, di- or trisubstituted by substituents independently selected from the group consisting of methyl, ethyl and hydroxymethyl.

2. A saccharine salt according to claim 1, in which A represents 2-decahydronaphthyl which is optionally mono- or disubstituted by substituents independently selected from the group consisting of methyl, ethyl, n- or i-propyl, n-, i-, s- or t-butyl, 2-methyl-but-2-yl, methoxy and ethoxy; or furthermore represents β-naphthyl which is optionally mono-, di- or trisubstituted by substituents independently selected from the group consisting of fluorine, chlorine, bromine, methyl, ethyl, n- or i-propyl, n-, i-, s- or t-butyl, 2-methyl-but-2-yl, methoxy and ethoxy.

3. A compound according to claim 1, wherein such compound is the saccharine salt of 1-(3-methyl-piperidin-1-yl)-2-methyl-3-β-naphthyl-propane of the formula

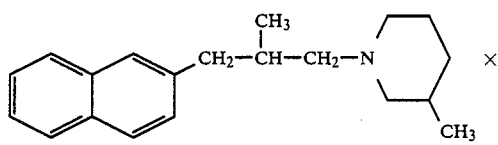

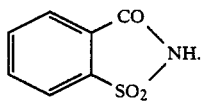

4. A compound according to claim 1, wherein such compound is the saccharine salt of 1-(2,6-dimethylmorpholin-4-yl)-2-methyl-3-(6-methyl-decahydronaphth-2-yl)-propane of the formula

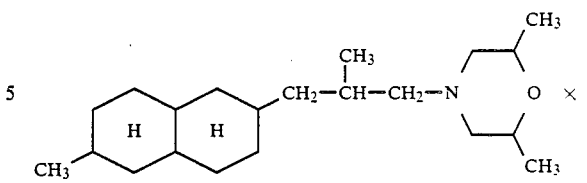

5. A compound according to claim 1, wherein such compound is the saccharine salt of 1-(3,5-dimethylpiperidin-1-yl)-2-methyl-3-(6-methyl-decahydronaphth-2-yl)-propane of the formula

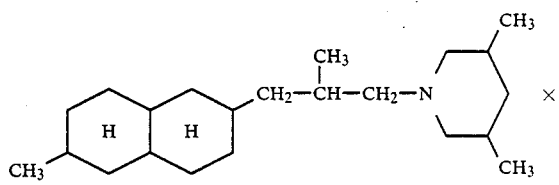

6. A fungicidal composition comprising a fungicidally effective amount of a saccharine salt according to claim 1 and a diluent.

7. A method of combating fungi which comprises applying to such fungi or to a fungus habitat a fungicidally effective amount of a saccharine salt according to claim 1.

8. The method according to claim 7 wherein such compound is the saccharine salt of
1-(3-methyl-piperidin-1-yl)-2-methyl-3-β-naphthyl-propane,
1-(2,6-dimethylmorpholin-4-yl)-2-methyl-3-(6-methyl-decahydronaphth-2-yl)-propane or
1-(3,5-dimethyl-piperidin-1-yl)-2-methyl-3-(6-methyl-decahydronaphth-2-yl)-propane.

* * * * *

UNITED STATES PATENT AND TRADEMARK OFFICE
CERTIFICATE OF CORRECTION

PATENT NO. : 4,829,063

DATED : May 9, 1989

INVENTOR(S) : Weissmuller et al

It is certified that error appears in the above-identified patent and that said Letters Patent is hereby corrected as shown below:

Title Page : FOREIGN PATENT DOCUMENTS  Add 0161455  11/1985  Great Britain
                                           0158074  10/1985  Great Britain Signed and Sealed this Tenth Day of July, 1990

Attest:

HARRY F. MANBECK, JR.

*Attesting Officer*  *Commissioner of Patents and Trademarks*